United States Patent
Higgins et al.

(10) Patent No.: US 12,121,842 B2
(45) Date of Patent: Oct. 22, 2024

(54) USE OF CLEAN AND DRY GAS FOR PARTICLE REMOVAL AND ASSEMBLY THEREFOR

(71) Applicant: Rapid Micro Biosystems, Inc., Lowell, MA (US)

(72) Inventors: Rich Higgins, Haverhill, MA (US); Ken Flaton, Harvard, MA (US)

(73) Assignee: RAPID MICRO BIOSYSTEMS, INC., Lowell, MA (US)

( * ) Notice: Subject to any disclaimer, the term of this patent is extended or adjusted under 35 U.S.C. 154(b) by 766 days.

(21) Appl. No.: 17/271,443

(22) PCT Filed: Aug. 29, 2019

(86) PCT No.: PCT/US2019/048873
§ 371 (c)(1),
(2) Date: Feb. 25, 2021

(87) PCT Pub. No.: WO2020/047295
PCT Pub. Date: Mar. 5, 2020

(65) Prior Publication Data
US 2021/0322912 A1    Oct. 21, 2021

Related U.S. Application Data

(60) Provisional application No. 62/724,376, filed on Aug. 29, 2018.

(51) Int. Cl.
*B01D 46/00*   (2022.01)
*B01D 53/26*   (2006.01)

(52) U.S. Cl.
CPC ....... *B01D 46/0027* (2013.01); *B01D 53/261* (2013.01); *B01D 53/263* (2013.01); *B01D 2258/06* (2013.01)

(58) Field of Classification Search
CPC ............. B01D 46/0027; B01D 53/261; B01D 53/263; B01D 2258/06; B01D 53/26;
(Continued)

(56) References Cited

U.S. PATENT DOCUMENTS 5,766,868 A * 6/1998 Seto .................... C12Q 1/04
                                                  210/650
5,862,439 A * 1/1999 Pozzanghera .......... G03G 21/00
                                                   399/92
(Continued)

FOREIGN PATENT DOCUMENTS

CN    106497779 A      3/2017
CN    111378567 A  *  7/2020  ............ C12M 23/00
(Continued)

OTHER PUBLICATIONS

Google translation of WO 2013/132630 (Year: 2013).*
(Continued)

*Primary Examiner* — Stephen Hobson
(74) *Attorney, Agent, or Firm* — GOODWIN PROCTER LLP

(57) ABSTRACT

The invention features particle removal assemblies and methods for removing dust and other debris from a sample container, e.g., to improve counting colonies of microorganisms (e.g., bacteria, fungi, or protists) present in environmental, pharmaceutical, biological, and other samples. An assembly of the invention includes components for particle removal, e.g., a filter, a dryer, a flow controller, and an outlet. The invention also provides methods of detecting samples after cleaning a sample container with clean and/or dry gas.

14 Claims, 3 Drawing Sheets

(58) Field of Classification Search
CPC .. B01D 53/268; G01N 35/00; G01N 15/0612; G01N 1/34; G01N 35/04; G01N 2035/0437; C12M 41/36; C12M 39/00
See application file for complete search history.

(56) References Cited

U.S. PATENT DOCUMENTS

| | | | | |
|---|---|---|---|---|
| 7,115,384 | B2 * | 10/2006 | Clark | G01N 21/253 435/31 |
| 9,057,046 | B2 * | 6/2015 | Browne | C12M 23/22 |
| 9,745,546 | B2 * | 8/2017 | Aviles | C12M 23/38 |
| 2004/0236063 | A1 * | 11/2004 | Suzuki | C08J 3/12 528/308 |
| 2006/0086249 | A1 * | 4/2006 | Burban | F15B 21/041 55/385.4 |
| 2010/0120133 | A1 * | 5/2010 | Walsh | B01L 3/5021 435/288.7 |
| 2010/0216183 | A1 * | 8/2010 | Okanojo | C12Q 1/66 435/288.7 |
| 2012/0131814 | A1 * | 5/2012 | Gibbel | F26B 5/12 901/14 |
| 2015/0072377 | A1 * | 3/2015 | Browne | C12M 23/38 435/297.1 |
| 2015/0131814 | A1 * | 5/2015 | Usher | G06F 3/017 381/123 |
| 2016/0115520 | A1 * | 4/2016 | Krishnamurthy | C12Q 1/24 435/306.1 |
| 2021/0223273 | A1 * | 7/2021 | Scial | G01N 15/1433 |
| 2023/0075029 | A1 * | 3/2023 | Roulston | C12N 1/10 |
| 2023/0332090 | A1 * | 10/2023 | Moriyama | C12M 29/06 |

FOREIGN PATENT DOCUMENTS

| | | | | |
|---|---|---|---|---|
| CN | 109540640 | B * | 10/2023 | B08B 9/093 |
| DE | 102010003507 | A1 * | 10/2011 | B01D 53/22 |
| JP | H0337547 | A | 2/1991 | |
| JP | 2000-078964 | * | 3/2000 | |
| JP | 2003229404 | A | 8/2003 | |
| JP | 2005502354 | A | 1/2005 | |
| JP | 2015514424 | A | 6/2016 | |
| KR | 20030039318 | A | 5/2003 | |
| KR | 100904278 | B1 | 6/2009 | |
| WO | WO-2013132630 | A1 * | 9/2013 | C12M 41/36 |
| WO | 2018001520 | A1 | 1/2018 | |
| WO | WO-2020047295 | A1 * | 3/2020 | B01D 46/0027 |

OTHER PUBLICATIONS

Epo translation of JP 2000-078964 (Year: 2000).*
Epo translation of DE102010003507 (Year: 2011).*
"Heatless desiccant dryers" Nortec published Nov. 2009 accessed at <https://www.nbdry.com/brochures/heatlessdesiccantdryers.pdf> (Year: 2009).*
"High Efficiency V Type Hepa Air Filter Dust 0.1um Porosity For Hepa Systems" published Jul. 21, 2017 accessed at <https://web.archive.org/web/20170721055545/https://www.cleanroom-airshower.com/sale-9028978-high-efficiency-v-type-hepa-air-filter-dust-0-1um-porosity-for-hepa-systems.html> (Year: 2017).*
International Search Report and Written Opinion of PCT Appln No. PCT/US2019/048873, mailed on Dec. 27, 2019.
International Preliminary Report on Patentability of PCT Appln No. PCT/US2019/048873, issued on Mar. 2, 2021, 6 pages.

* cited by examiner

USE OF CLEAN AND DRY GAS FOR PARTICLE REMOVAL AND ASSEMBLY THEREFOR

BACKGROUND OF THE INVENTION

In many industries, particularly the food, beverage, healthcare, electronic, and pharmaceutical industries, it is essential to analyze samples rapidly for the degree of contamination by microorganisms, such as bacteria, yeasts, or molds.

One microbial culture technique, called microbial enumeration or colony counting, quantifies the number of microbial cells in a sample. The microbial enumeration method, which is based on in situ microbial replication, generally yields one visually detectable "colony" for each microbial cell in the sample. Thus, counting the visible colonies allows microbiologists to accurately determine the number of microbial cells in a sample. To perform microbial enumeration, bacterial cells can be dispersed on the surface of nutrient agar in Petri dishes ("agar plates") and incubated under conditions that permit in situ bacterial replication. Microbial enumeration is simple, ultra-sensitive, inexpensive, and quantitative but may also be slow. Colonies can be digitally imaged; however, in certain instances, dust and other debris may make colony counting more difficult.

Accordingly, there is a need for detection devices that include components to remove dust and other debris from sample containers for rapid and accurate microbial enumeration of the samples.

SUMMARY OF THE INVENTION

The invention provides a particle removal assembly. The assembly may be used for removing dust and other debris from a sample container, e.g., for accurate microbial enumeration of the sample, e.g., an environmental sample.

In one aspect, the invention provides a particle removal assembly including a filter, e.g., a 0.01 micron filter; a dryer, e.g., membrane dryer; a flow controller, e.g., valve; and an outlet, e.g., blow off nozzle. In the assembly, gas flows through the filter, dryer, and outlet, and the flow controller controls the rate of flow through the assembly. The particle removal assembly can be used to remove dust and other debris from a sample container, e.g., the lid, bottom, or other portion being imaged, prior to detection of the sample. In one embodiment, the filter is upstream, i.e., closer to the inlet, from the dryer and/or the dryer is upstream from the flow controller, e.g., gas flows from a source through the filter to the dryer to the outlet. The flow controller may be placed in any appropriate position, e.g., between the dryer and the outlet, to control the flow of gas through the assembly.

In certain embodiments, the outlet, e.g., blow-off nozzle, includes a plurality of openings. In embodiments, the filter is selected from the group consisting of fiber filters, polymer filters, paper filters, metal mesh filters, membranes, activated carbon, an electrostatic precipitator, or a combination thereof. The filter may have a porosity of $\leq 0.1$ µm. In embodiments, the dryer is selected from the group consisting of evaporative dryers, membrane dryers, absorption dryers, adsorption dryers, or a combination thereof. The assembly may further include a reservoir for storage of the gas upstream of the outlet, e.g., where the reservoir is downstream of the filter and dryer. In embodiments, after passing through the filter and dryer, the gas has $\leq 90{,}000$ particles/m$^3$ sized 0.5-1 µm, and $\leq 1000$ particles/m$^3$ sized 1-5 µm, the gas has a vapor pressure dew point of $\leq -20°$ C., and/or the gas has an amount of total oil of $\leq 0.1$ mg/m$^3$. In some embodiments, the particle removal assembly removes at least 50% (e.g., at least 55%, 60%, 65%, 70%, 75%, 80%, 85%, 90%, 95%, or 99%) of dust and other particles from a sample container, e.g., the imageable surface of the sample container. In some embodiments, the dryer removes at least 60% by mass (e.g., at least 65%, 70%, 75%, 80%, 85%, 90%, 95%, or 99%) of water or other liquids in the gas.

In another aspect, the invention provides a sample imaging device that includes an imager and a particle removal assembly including an outlet, e.g., a blow off nozzle, configured to direct gas to a sample container prior to imaging. In embodiments, the gas has 90,000 particles/m$^3$ sized 0.5-1 µm and $\leq 1000$ particles/m$^3$ sized 1-5 µm, e.g., where the gas has a vapor pressure dew point of $\leq -20°$ C. and/or an amount of total oil of $\leq 0.1$ mg/m$^3$. The imaging device may further include an incubator, in which the sample container is stored before imaging.

The invention also provides a sample imaging device including an imager and a particle removal assembly as described herein. The device may further include an incubator.

In another aspect, the invention provides a method of detecting a sample, e.g., for microbial enumeration. The method includes applying a volume of clean and/or dry gas, e.g., air, nitrogen, or argon, to the surface of a sample container for a time sufficient to remove particulate matter, e.g., for no more than 10 s, e.g., no more than 5 s, 3 s, 2 s, 1 s, or 0.5 s, and detecting, e.g., imaging, the sample in the sample container. In certain embodiments, the mass concentration of particulate matter in the gas is less than 30 µg/m$^3$, e.g., less than 10, 5, 1, 0.5, 0.1, 0.005, 0.001, 0.0005, 0.0001, 0.00005, or 0.00001 µg/m$^3$ and/or the particle number concentration is below 20,000 particles/cm$^3$, e.g., less than 10,000, 5,000, 1000, 500, 100, 50, 10, 5, 1, 0.5, 0.1, 0.05, or 0.01 particles/cm$^3$. Alternatively or in addition, the gas has less than 100 ppm of a liquid, e.g., water, e.g., less than 50, 10, 7, 5, 3, 2, 1, 0.5, 0.2, 0.01, or 0.001 ppm of the liquid, e.g., water. For example, the gas may include 20,000 particles/m$^3$ sized 0.1-0.5 µm, $\leq 400$ particles/m$^3$ sized 0.5-1 µm, and $\leq 10$ particles/m$^3$ sized 1-5 µm; have a vapor pressure dew point of $\leq -20°$ C., e.g., $\leq -40°$ C. or $-70°$ C.; and contain total oil (aerosol and vapor) of $\leq 0.1$ mg/m$^3$, e.g., $\leq 0.01$ mg/m$^3$.

The invention provides a method of detecting colonies in a sample by actuating a particle removal assembly as described herein to remove particles from a surface of a sample container containing the sample and imaging the sample in the sample container. The invention provides a method of detecting colonies in a sample by actuating a gas source to remove particles from a surface of a sample container containing the sample and imaging the sample in the sample container, wherein the gas has $\leq 90{,}000$ particles/m$^3$ sized 0.5-1 µm, and $\leq 1000$ particles/m$^3$ sized 1-5 µm, e.g., where the gas has a vapor pressure dew point of $\leq -20°$ C. and/or a total amount of oil of $\leq 0.1$ mg/m$^3$. In embodiments, the sample includes microbes, and the method further includes quantifying the number of microbial colonies in the sample. In embodiments, the method further includes imaging the sample more than once, wherein the sample is incubated between imagings.

In yet another aspect, the invention provides a method of detecting a sample, e.g., for microbial enumeration. The method includes actuating a particle removal assembly to remove particulate matter from a sample container and detecting, e.g., imaging, the sample in the sample container.

Other features and advantages will be apparent from the following description, the drawings, and the claims.

DETAILED DESCRIPTION OF THE INVENTION

The invention features particle removal assemblies and methods for removing dust and other debris from a sample container, e.g., to improve counting colonies of microorganisms (e.g., bacteria, fungi, or protists) present in environmental, pharmaceutical, biological, and other samples. An assembly of the invention includes components for particle removal, e.g., a filter, a dryer, a flow controller, and an outlet.

Particle Removal Assembly

Dust and other particles (e.g., solid particles, water, or oil) on a sample container can interfere with accurate detection, e.g., imaging, of the sample, e.g., for microbial enumeration. The particle removal assemblies of the invention help reduce false positives in colony counting by removing dust and other debris from the portion of the sample container, e.g., lid or bottom, through which detection, e.g., imaging, occurs. In particular, the assemblies, devices, and methods are of particular use in eliminating moveable particles that may change position when a sample container is imaged multiple times.

Figure 1:
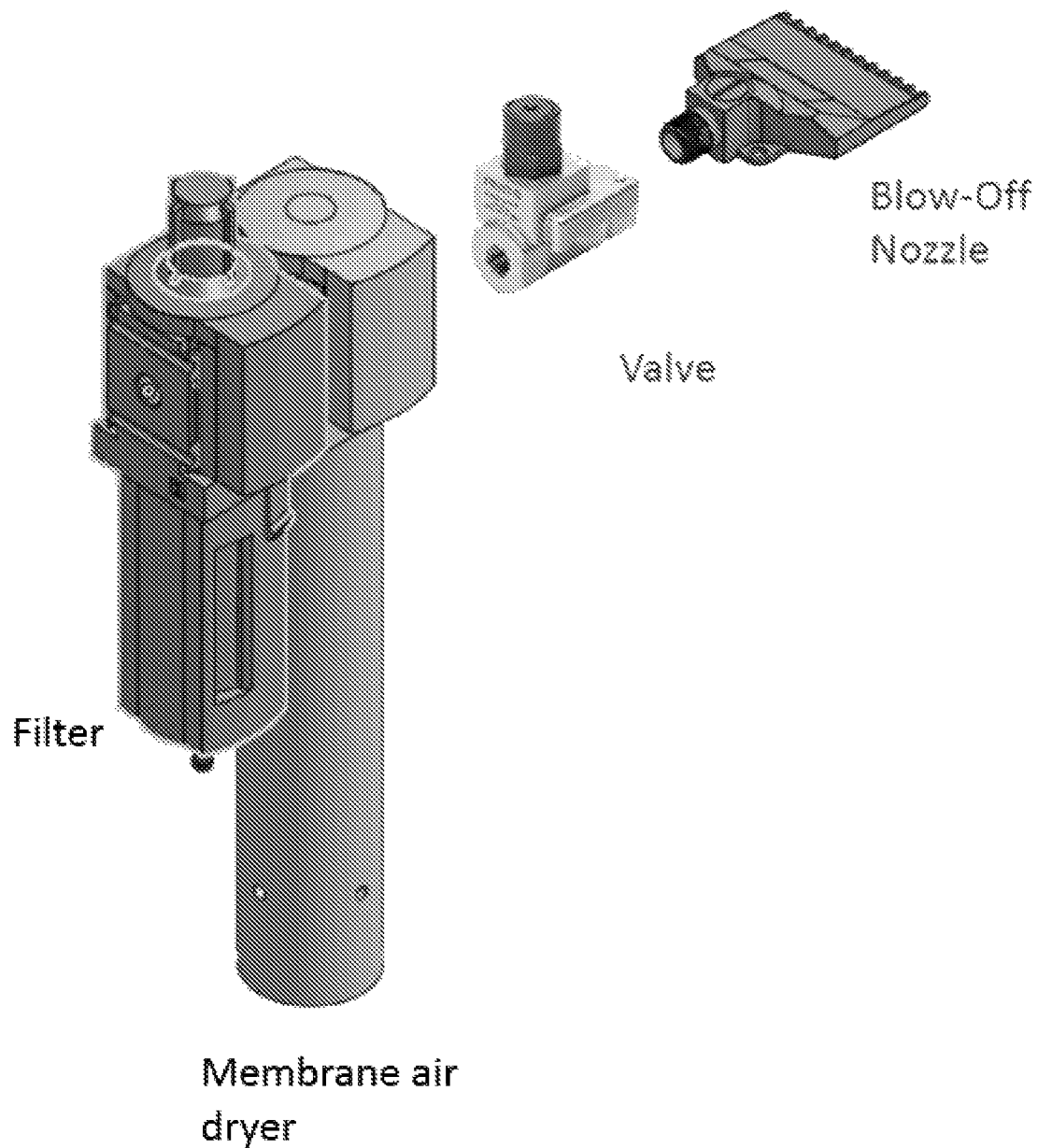
FIG. 1 is an illustration of an exploded view of a particle removal assembly of the invention that includes a filter, a dryer, e.g., membrane dryer, a flow controller, e.g., valve, and an outlet, e.g., blow-off nozzle.
Figure 2:
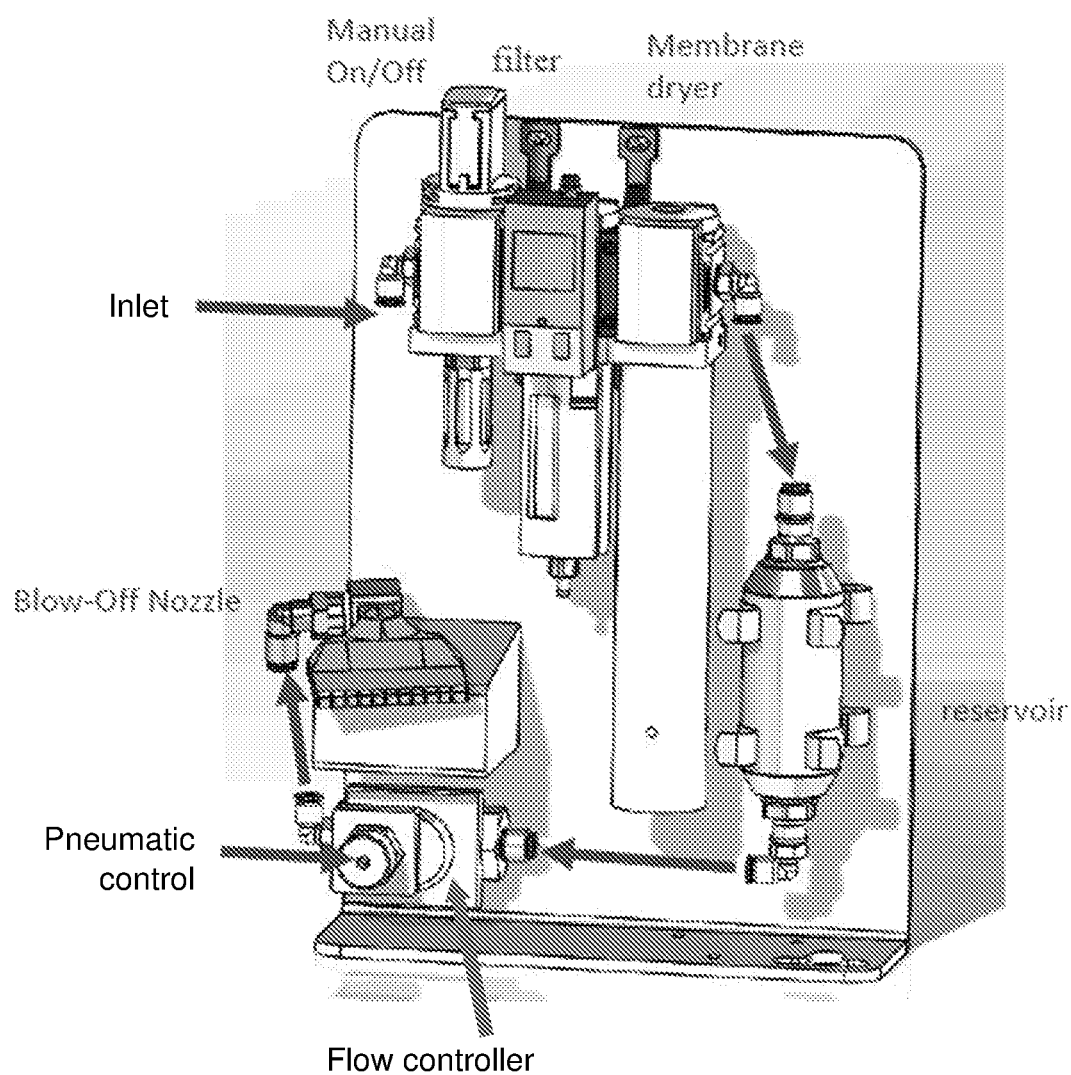
FIG. 2 is an illustration of a particle removal assembly of the invention that includes a reservoir for gas, a filter, a dryer, e.g., membrane dryer, a flow controller, e.g., valve, and an outlet, e.g., blow-off nozzle.

A particle removal assembly of the invention may include a filter, a dryer, e.g., a membrane dryer, a flow controller, e.g., a valve, and an outlet, e.g., a blow-off nozzle. It will be understood that a gas inlet is also present. Exemplary assemblies are shown in FIGS. 1 and 2. The filter (e.g., a 0.01 μm filter) removes particles from the gas, e.g., air, argon, or nitrogen, flowing through. The dryer removes water and other liquids from the gas. The outlet, e.g., blow-off nozzle, directs the filtered, dried gas to a surface of a sample container, e.g., lid, to remove dust and other debris from it. The filter and the dryer ensure the quality of the gas being used for particle removal. If the source of the gas is otherwise free of particles and/or sufficiently dry, one or more of these components may be omitted from the assembly. Suitable gases include air, nitrogen, and argon.

In some cases, the filter may be any filter suitable for the removal of particulate matter from a gas. Examples of filters include, but are not limited to, fiber filters, e.g., layered fiberglass or cotton, polymer filters, e.g., polyester or polyurethane, paper filters, metal mesh filters, membranes, activated carbon, or combinations thereof, e.g., a High Efficiency Particulate Air (HEPA) filter. Alternatively or in addition, a filter may include electrostatic precipitation to remove particles from the gas. Other filters are known in the art. A particle removal assembly of the present invention may include two or more filters, e.g., in series, with each filter being of the same or a different type and/or having different porosities for capturing different size particles. For example, a filter useful for the present invention may have a first stage for the removal of coarse particles, i.e., those with a diameter greater than 10 μm, and have successive stages to remove finer particles from the gas.

Filters useful for the present invention may have pore sizes from 100 μm to 0.001 μm, e.g., from 100 μm to 10 μm, from 50 μm to 5 μm, from 10 μm to 1 μm, from 10 μm to 0.001 μm, from 5 μm to 0.5 μm, from 1 μm to 0.1 μm, from 1 μm to 0.001 μm, from 0.5 μm to 0.05 μm, 0.1 μm to 0.001 μm, 0.05 μm to 0.005 μm, or from 0.01 μm to 0.001 μm. An exemplary filter for the present invention has a pore size of 0.01 μm.

The filter of the particle removal assembly of the invention may remove at least 50% of the particulate matter from the gas, e.g., at least 50%, at least 55%, at least 60%, at least 65%, at least 70%, at least 75%, at least 80%, at least 85%, at least 90%, at least 95%, at least 96%, at least 97%, at least 98%, at least 99%, at least 99.5%, at least 99.95%, at least 99.995%, at least 99.9995%, at least 99.99995%, or at least 99.999995% of particulate matter from the gas. Alternatively or in addition, the filter (or filters) reduces the mass concentration of particulate matter to less than 30 μg/m$^3$, e.g., less than 10, 5, 1, 0.5, 0.1, 0.005, 0.001, 0.0005, 0.0001, 0.00005, or 0.00001 μg/m$^3$ and/or reduces the particle number concentration to below 20,000 particles/cm$^3$, e.g., less than 10,000, 5,000, 1000, 500, 100, 50, 10, 5, 1, 0.5, 0.1, 0.05, 0.02, 0.01, 0.005, 0.002, or 0.001 particles/cm$^3$.

Examples of dryers include, but are not limited to, evaporative dryers, membrane dryers, absorption dryers, e.g., halide or sulfate salt dryers, adsorption dryers, e.g., activated carbon, silica gel, activated alumina, or molecular sieves, or combinations thereof. Other gas dryers are known in the art. An exemplary dryer for a particle removal assembly of the present invention is a membrane dryer. A particle removal assembly of the present invention may include two or more dryers, e.g., in series, with each dryer being of the same or different type of dryer and/or configured to capture different liquids from the gas. For example, a dryer useful for the present invention may include a first stage to remove residual organic liquids from the gas and a second stage to remove water vapor from the gas. In addition, a dryer may be temperature controlled to reduce the temperature of the gas exiting the dryer, e.g., to reduce further uptake of liquid into the dried gas.

The dryer of the particle removal assembly of the invention may remove at least 50% by mass of liquid from the input gas, e.g., at least 50%, at least 55%, at least 60%, at least 65%, at least 70%, at least 75%, at least 80%, at least 85%, at least 90%, at least 95%, at least 96%, at least 97%, at least 98%, at least 99%, at least 99.5%, at least 99.95%, at least 99.995%, at least 99.9995%, at least 99.99995%, or at least 99.999995% of liquid by mass from the gas. In certain embodiments, the dryer removes at least 50% by mass of water from the input gas, e.g., at least 50%, at least 55%, at least 60%, at least 65%, at least 70%, at least 75%, at least 80%, at least 85%, at least 90%, at least 95%, at least 96%, at least 97%, at least 98%, at least 99%, at least 99.5%, at least 99.95%, at least 99.995%, at least 99.9995%, at least 99.99995%, or at least 99.999995% of water by mass from the gas. Alternatively or in addition, the dryer (or dryers) produces a gas having less than 10 ppm of a liquid, e.g., water, e.g., less than 100, 50, 10, 7, 5, 3, 2, 1, 0.5, 0.2, 0.01, or 0.001 ppm of the liquid, e.g., water.

The particle removal assembly may also produce air according to ISO8573-1:2010. For example, the particle removal assembly may produce air of class 3:3:2, 3:2:2:, 3:1:2:, 3:3:1, 3:2:1, 3:1:1, 2:3:2, 2:2:2:, 2:1:2, 2:3:1, 2:2:1, 2:3:1, 2:1:1, 1:3:2, 1:2:2, 1:1:2, 1:1:1, or 1:3:1, e.g., from air of class 7:4:4 or 6:4:4. In another example, the particle removal assembly produces a gas other than air having the particle and water qualities of these classes. Accordingly, the particle removal assembly may produce gas with ≤90,000 particles/m$^3$ sized 0.5-1 μm and ≤1000 particles/m$^3$ sized 1-5 μm, such as 400,000 particles/m$^3$ sized 0.1-0.5 μm, ≤6,000 particles/m$^3$ sized 0.5-1 μm and ≤100 particles/m$^3$ sized 1-5 μm (e.g., 20,000 particles/m$^3$ sized 0.1-0.5 μm, ≤400 particles/m$^3$ sized 0.5-1 μm, and 10 particles/m$^3$ sized 1-5 μm); the gas produced may have a vapor pressure dew point of ≤−20° C., e.g., ≤−40° C. or −70° C.; and/or the gas produced may contain an amount of total oil (aerosol and vapor) of ≤0.1 mg/m$^3$, e.g., ≤0.01 mg/m$^3$.

A particle removal assembly of the invention may include a reservoir. The reservoir may be disposed downstream of the filter and/or the dryer. The reservoir may be used to store the clean and/or dry gas to ensure even and consistent flow of gas from the outlet.

The flow controller of the particle removal assembly of the invention includes a valve that controls the presence, absence, and/or flow rate of gas exiting the outlet. The flow controller may be located in any suitable position, such as between the filter and/or dryer and the outlet of the assembly. The valve of the flow controller may be any suitable valve for controlling or regulating gas flow, including, but not limited to, butterfly valves, diaphragm valves, globe valves, needle valves, or poppet valves. Other suitable valves are known in the art. The operation of the valve may be controlled externally, such as with a computer-implemented program that controls the operations of an instrument, e.g., the GROWTHDIRECT® system for rapid colony counting (Rapid Micro Biosystems, Lowell, MA), such that the gas is delivered at the desired time during a measurement.

The outlet, e.g., blow off nozzle, of the particle removal assembly of the invention directs the clean and dried gas onto surfaces that may be contaminated with particulates to remove them from the surface. The outlet, e.g., blow off nozzle, may have one or more openings for directing gas flow and further may have a size and shape suitable to ensure that the gas exiting the outlets has dimensions to remove particles from the entire desired area of the sample container. For example, as shown in FIGS. 1 and 2, the outlet, i.e., blow off nozzle, has a plurality of openings spanning a linear dimension perpendicular to the direction of gas flow. A skilled artisan will appreciate that the size, shape, and number of openings in the outlet may be altered based on the size and shape of the sample container.

Sample Imaging Device

In one aspect of the invention, the particle removal assembly is useful in automated detection of microorganisms, e.g., using the GROWTHDIRECT® system or as described in U.S. Pat. No. 7,582,415. Suitable sample containers include Petri dishes and similar containers such as those described in U.S. Pat. Nos. 9,057,046, 9,745,546, and 2015/0072377. In particular, the particle removal assembly is useful in removing dust and other debris from sample containers that include microbial growth media with microbes growing on the media or on a membrane in contact with the media by directing a volume of pressurized clean and dried gas onto the sample container, e.g., the lid. The detection may include detection of labels or detection of intrinsic properties of microbes, e.g., autofluorescence.

Figure 3:
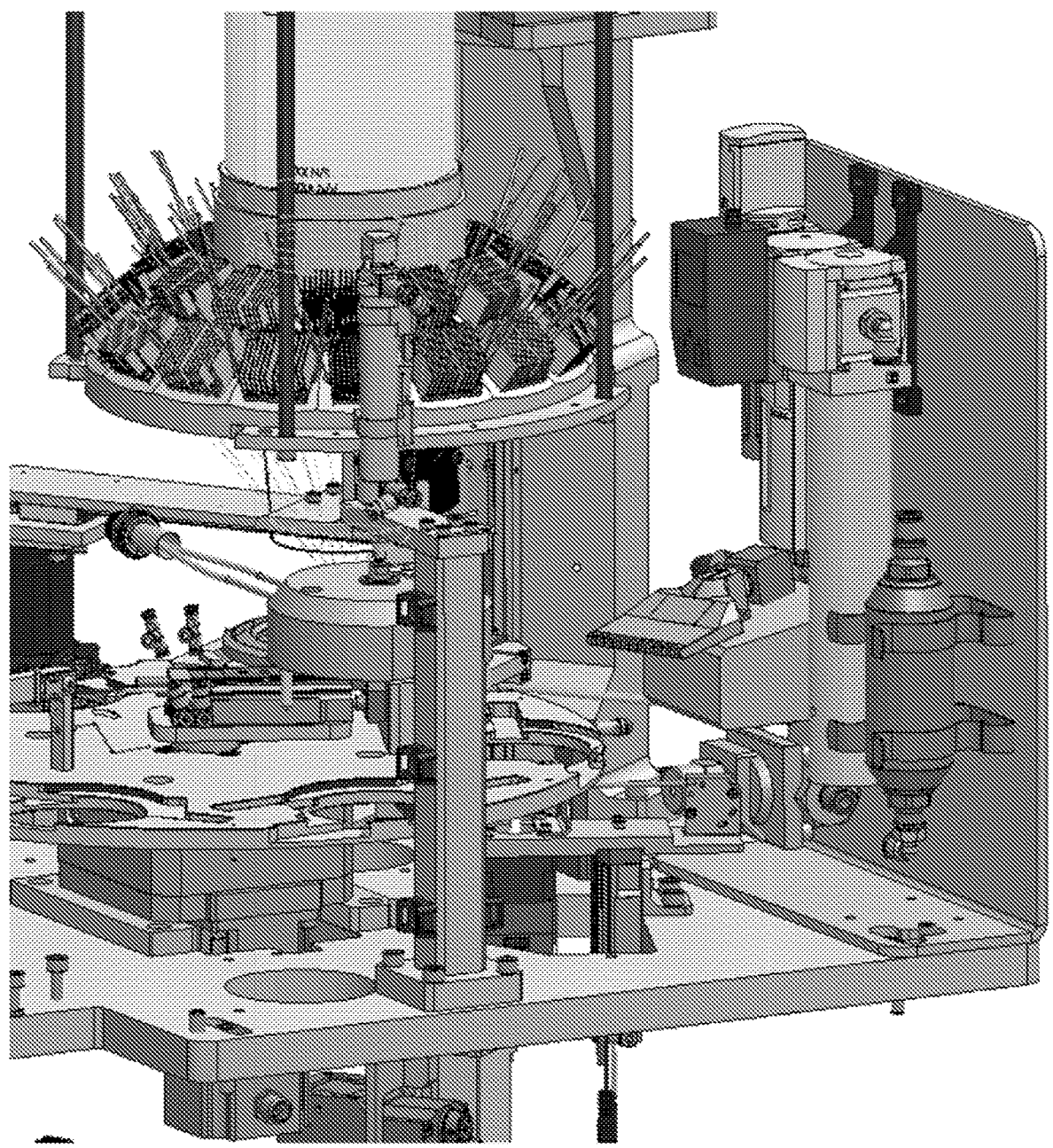
FIG. 3 is a schematic depiction from the side view of a sample imaging device that includes a particle removal assembly of the invention.

The invention also provides a sample imaging device that includes an imager and a particle removal assembly including an outlet, e.g., a blow off nozzle, configured to direct gas to a sample container prior to imaging. An exemplary sample imaging device is shown in FIG. 3. As shown, the device includes a turntable capable of holding a plurality of sample containers that rotates each sample container towards an imaging position. The particle removal assembly is positioned so that the sample container can be cleared of particles prior to imaging using a volume of pressurized clean and dried gas. Once cleared of particulates, the sample container may be imaged. The sample imaging device may also include an incubator for growth of microbes, and the sample imaging device may be configured to allow imaging of a sample container at various times during incubation, e.g., with each imaging being preceded by the clearing of particles on the sample container using the particle removal assembly.

The sample imaging device may further include an air flow, e.g., at least 5, 10, or 100 cfm, such as 5-1000 cfm, 10-100 cfm, 250-750 cfm, or 500-600 cfm, to sweep any particulate matter removed from sample containers out of the imaging device.

Methods of Use

The invention provides methods of cleaning a sample container to remove particulate matter prior to detection, e.g., imaging. The method includes applying a volume of clean and/or dry gas, e.g., air, nitrogen, or argon, to the surface of the sample container for a time sufficient to remove particulate matter, e.g., for no more than 10 s, e.g., no more than 5 s, 3 s, 2 s, 1 s, or 0.5 s, e.g., between 0.1-10 s or 0.5-5 s. In certain embodiments, the mass concentration of particulate matter in the gas is less than 30 μg/m$^3$, e.g., less than 10, 5, 1, 0.5, 0.1, 0.005, 0.001, 0.0005, 0.0001, 0.00005, or 0.00001 μg/m$^3$ and/or the particle number concentration is below 20,000 particles/cm$^3$, e.g., less than 10,000, 5,000, 1000, 500, 100, 50, 10, 5, 1, 0.5, 0.1, 0.05, or 0.01 particles/cm$^3$. Alternatively or in addition, the gas has less than 100 ppm of a liquid, e.g., water, e.g., less than 50, 10, 7, 5, 3, 2, 1, 0.5, 0.2, 0.01, or 0.001 ppm of the liquid, e.g., water. The clean and dry gas may be air according to ISO8573-1:2010, e.g., air of class 1:3:2, 1:2:2, 1:1:2, or 1:3:1, or other gas with equivalent properties. For example, the gas may include ≤90,000 particles/m$^3$ sized 0.5-1 μm and ≤1000 particles/m$^3$ sized 1-5 μm, such as ≤400,000 particles/m$^3$ sized 0.1-0.5 μm, 6,000 particles/m$^3$ sized 0.5-1 μm and 100 particles/m$^3$ sized 1-5 μm (e.g., 20,000 particles/m$^3$ sized 0.1-0.5 μm, ≤400 particles/m$^3$ sized 0.5-1 μm, and ≤10 particles/m$^3$ sized 1-5 μm); have a vapor pressure dew point of ≤−20° C., e.g., −40° C. or −70° C.; and/or contain an amount of total oil (aerosol and vapor) of ≤0.1 mg/m$^3$, e.g., ≤0.01 mg/m$^3$.

The clean and/or dry gas may be produced by a particle removal assembly described herein.

The rate of gas delivery may be any suitable rate for dust removal, e.g., at most 1000, 500, or 100 cfm, e.g., at most 50, 10, 5, 1, 0.5, 0.3, or 0.1 cfm, e.g., between 0.0001-1000 cfm, 0.0001-500 cfm, 0.0001-100 cfm, 0.0001-50 cfm, 0.0001-10 cfm, 0.0001-5 cfm, 0.0001-1 cfm, or 0.0001-0.1 cfm, 0.001-100 cfm, 0.001-50 cfm, 0.001-10 cfm, 0.001-5 cfm, 0.001-1 cfm, or 0.001-0.1 cfm, 0.01-100 cfm, 0.01-50 cfm, 0.01-10 cfm, 0.01-5 cfm, 0.01-1 cfm, or 0.01-0.1 cfm, 0.1-100 cfm, 0.1-50 cfm, 0.1-10 cfm, 0.1-5 cfm, or 0.1-1 cfm. The pressure of the gas at the outlet may be any suitable pressure, e.g., at most 25 bar, e.g. at most 20, 15, 10, 5, or 3 bar, e.g., between 1-25, 1-20, 1-15, 1-10, 1-5, 1-3, 1.5-25, 1.5-20, 1.5-15, 1.5-10, 1.5-5, or 1.5-3 bar.

The clean and/or dry gas, e.g., produced using a particle removal assembly described herein, facilitates accurately counting colonies in a sample by reducing the number of false positives that can be produced by dust and other debris on a surface of the sample container. For example, use of the clean and/or dry gas, e.g., produced by a particle removal assembly, prior to detection, e.g., imaging, may reduce the number of false positives by a factor of at least 2, 5, 10, 15, 20, 25, 50, 75, 100, 250, 500, 750, or 1000, e.g., by a factor of 5-500, 5-100, 5-50, 5-25, or 5-20. The use of clean and/or dry gas, e.g., produced by a particle removal assembly, may be particularly useful when detecting microcolonies, e.g., microcolonies sized below 1000, 750, 500, 250, 100, 75, or 50 µm in diameter (or in two orthogonal dimensions). Detection may be repeated to discern growing colonies from non-growing microorganisms, e.g., with each repeated imaging being preceded by the clearing of particles on the sample container, e.g., using a particle removal assembly. When multiple detections are employed, the sample container may be incubated or stored between detections, e.g., in a closed incubation chamber. The sample container may further be transferred between the incubator or storage area, the location of particulate matter removal, and detection (if different from particulate matter removal) using an automated system. Such a system may further analyze the data acquired from detection, e.g., to count the number of microbial colonies.

Detection of the colonies may occur by any appropriate method and may be based on labels in the cells or media or on an intrinsic optical property of the cells, e.g., autofluorescence. Detection typically occurs by optical imaging using a camera.

Sample containers may be of any appropriate size as described herein. In addition, the area of the sample container to be contacted with gas may have a cross-sectional dimension of between 1 mm and 100 mm, e.g., between 10 mm and 80 mm; the area may have the same extent in two orthogonal dimensions. The area to be detected may be polygonal, e.g., square, round, elliptical, or any other shape.

After sample collection and installation of the sample container in a sample imaging device, e.g., the GROWTH-DIRECT® system for rapid colony counting, clean and/or dry gas, e.g., from a particle removal assembly of the invention, may be used to remove dust and other debris from the sample container before detection of colonies in the sample. In some embodiments, a particle removal assembly directs a volume of clean and dried gas onto the sample container. An automated system may detect the presence of the sample container in a position for imaging, the controller of the automated system communicates with the flow controller of the particle removal assembly to open the valve of the flow controller and discharge a volume of gas from the outlet, e.g., blow off nozzle, onto the sample container.

Other methods and instruments for manual or automated colony counting that can be used with the particle removal assembly of the present invention are known in the art.

EXAMPLE

One example of a particle removal assembly is shown in FIGS. 2 and 3. In this example, air from an external source is introduced into the particle removal assembly. The assembly includes a manual on/off valve. Air entering the assembly passes through a 0.01 filter and a membrane dryer (Festo). Air exiting the dryer is stored in a 0.4 l reservoir (Festo). A pneumatically controlled poppet valve (Festo) controls emission of the air from a blow off nozzle (Mc-Master-Carr). The tubing connections between components are not shown but can be of any suitable material, e.g., plastic or metal. FIG. 3 shows the particle removal assembly in the GROWTHDIRECT® system for rapid colony counting. Use of the particle removal assembly with the GROWTHDIRECT® system for rapid colony counting reduced the number of false positives from 2-3/1000 to 1-2/10,000.

Other embodiments are in the claims.

What is claimed is:

1. A particle removal assembly comprising:
   (a) a filter configured to remove particulate matter from a gas;
   (b) a dryer;
   (c) a flow controller;
   (d) an outlet, wherein the outlet is a blow-off nozzle; and
   (e) a reservoir for storage of the gas,
   wherein:
   the filter, dryer, flow controller, and outlet are connected in series to allow the gas to flow through the filter, dryer, and outlet, the flow controller controls the rate of flow through the outlet, and the reservoir is provided upstream of the outlet and downstream of the filter and dryer.

2. The assembly of claim 1, wherein the filter is upstream from the dryer.

3. The assembly of claim 1, wherein the dryer is upstream from the flow controller.

4. The assembly of claim 1, wherein the blow-off nozzle comprises a plurality of openings.

5. The assembly of claim 1, wherein the filter is selected from the group consisting of fiber filters, polymer filters, paper filters, metal mesh filters, membranes, activated carbon, an electrostatic precipitator, or a combination thereof.

6. The assembly of claim 1, wherein the dryer is selected from the group consisting of evaporative dryers, membrane dryers, absorption dryers, adsorption dryers, or a combination thereof.

7. The assembly of claim 1, wherein the filter has a porosity of ≤0.1 µm.

8. The assembly of claim 1, wherein, after passing through the filter and dryer, the gas has ≤90,000 particles/$m^3$ sized 0.5-1 µm and ≤1000 particles/$m^3$ sized 1-5 µm.

9. The assembly of claim 1, wherein, after passing through the filter and dryer, the gas has a vapor pressure dew point of ≤−20° C.

10. The assembly of claim 1, wherein, after passing through the filter and dryer, the gas has an amount of total oil of ≤0.1 mg/$m^3$.

11. The assembly of claim 1, wherein the flow controller comprises a valve configured to regulate the flow of the gas.

12. A sample imaging device comprising:
    (a) an imager; and
    (b) the particle removal assembly of claim 1.

13. The device of claim 12, further comprising an incubator.

14. A method of detecting colonies in a sample comprising actuating the assembly of claim 1 to remove particles from a surface of a sample container containing the sample and imaging the sample in the sample container.

* * * * *